United States Patent [19]

Praefcke et al.

[11] Patent Number: 4,578,210

[45] Date of Patent: Mar. 25, 1986

[54] CARBOCYCLIC SIX-MEMBERED RING COMPOUNDS

[75] Inventors: Klaus Praefcke; Bernd Kohne; Wadi Poules, all of Berlin; Rudolf Eidenschink, Münster; Bernhard Scheuble, Alsbach-Hähnlein, all of Fed. Rep. of Germany

[73] Assignee: Merck Patent Gesellschaft mit beschränkter Haftung, Darmstadt, Fed. Rep. of Germany

[21] Appl. No.: 650,015

[22] Filed: Sep. 13, 1984

[30] Foreign Application Priority Data

Sep. 13, 1983 [DE]  Fed. Rep. of Germany ....... 3332955

[51] Int. Cl.$^4$ ............................ G02F 1/13; C09K 3/34
[52] U.S. Cl. ................. 252/299.6; 252/299.5; 252/299.63; 350/350 R; 560/1; 560/76; 560/144; 568/27; 568/28; 568/57; 568/648
[58] Field of Search ............ 252/299.6, 299.5, 299.63; 350/350 R; 560/1; 568/28

[56] References Cited

U.S. PATENT DOCUMENTS 4,333,709  6/1982  Dubois et al. ............... 252/299.4
4,430,650  2/1984  Billard et al. .............. 252/299.62

FOREIGN PATENT DOCUMENTS 42-19119  9/1967  Japan ........................ 560/1
46-2813   1/1971  Japan ........................ 560/1

OTHER PUBLICATIONS

C.A. 65, 20415f (1966).
C.A. 65, 20415e (1966).
Le Barny, P., et al., *Liquid Crystals and Ordered Fluids*, vol. 4, Edited by Griffin, A., et al., Plenum Press, N.Y., pp. 57-74, (1984).
Dubois, J. C., et al., *Liquid Crystals and Ordered Fluids*, vol. 4, Edited by Griffin, A., et al., Plenum Press, N.Y., pp. 1043-1060, (1984).
Destrade, C., et al., *Mol. Cryst. Liq. Cryst.*, vol. 71, pp. 111-135 (1981).
Tinh, N. H., et al., *Mol. Cryst. Liq. Cryst.*, vol. 68, pp. 101-111, (1981).
Destrade, C., et al., *J. De Physique*, Coll C3, Suppl. No. 4, vol. 40., pp. C3-17-C3-21 (1979).
Goozner, R. E., et al., *Mol. Cryst. Liq. Cryst.*, vol. 56 (Letters), pp. 75-81 (1979).
Chandrasekhar, S., *Advances in Liquid Crystals*, vol. 5, Edited by Brown, G. H., Academic Press, N.Y., pp. 47-78 (1982).
*Aldrich Catalog/Handbook of Fine Chemicals*, pp. 1151-1152, 1982-1983.
S. Chandrasekhar, *Mol. Cryst. Liq. Cryst.* 1981, vol. 63, pp. 171-180.

*Primary Examiner*—Teddy S. Gron
*Attorney, Agent, or Firm*—Millen & White

[57] ABSTRACT

Six-membered ring compounds of the formula I

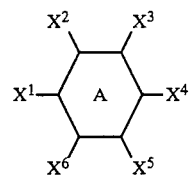

wherein
A is a benzene or cyclohexane ring,
$X^1$ to $X^6$ independently of one another in each case are H, —OR, —COOR, —SR, —SOR, —SO$_2$R or, if A is a cyclohexane ring, also —O—COR, and
R is in each case an alkyl group which has up to 15 C atoms and in which one or two CH$_2$ groups can be replaced by O atoms, at least three of the substituents $X^1$ to $X^6$ being other than H, can be used as constituents of discotic liquid-crystal phases for liquid-crystal display elements.

10 Claims, No Drawings

CARBOCYCLIC SIX-MEMBERED RING COMPOUNDS

This invention relates to new compounds especially useful as components of discotic, liquid-crystal phases.

SUMMARY OF THE INVENTION

It is an object of this invention to provide new stable liquid-crystal or mesogenic compounds which are suitable for use as components of discotic, liquid-crystal phases.

Upon further study of the specification and appended claims, further objects and advantages of this invention will become apparent to those skilled in the art.

These objects have been achieved by providing six-membered ring compounds of the formula I

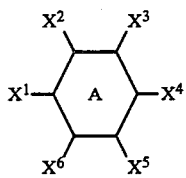

wherein
A is a benzene or cyclohexane ring,
$X^1$ to $X^6$ independently of one another in each case are H, —OR, —COOR, —SR, —SOR, —SO$_2$R or, if A is a cyclohexane ring, also —O—COR, and
R is in each case an alkyl group which has up to 15 C atoms and in which one or two non-adjacent CH$_2$ groups can be replaced by O atoms,
at least three of the substituents $X^1$ and $X^6$ being other than H.

In the test which follows, for the sake of simplicity, "Ph" is a benzene nucleus having six free valencies and "Cy" is a cyclohexane-1,2,3,4,5,6-hexayl group.

Similar compounds, namely hexaalkanoyloxybenzenes (corresponding to formula I, A is a benzene ring and $X^1$ and $X^2$ are —O—COR) are known (cf. S. Chandrasekhar, *Mol. Cryst. Liq. Cryst.* 63, (1981) 171-179 and the literature quoted therein).

Like similar compounds, the compounds of the formula I can be used as components of discotic, liquid-crystal phases, especially for displays which are based on the guest-host effect, the effect of deformation of aligned phases, the effect of dynamic scattering or on a change in the ellipticity of light.

DETAILED DISCUSSION

It has been found that the compounds of the formula I are excellently suitable for use as components of discotic, liquid-crystal phases. In particular, stable, discotic, liquid-crystal phases having a wide mesophase temperature range which is advantageously situated for electrooptical effects can be prepared with their aid.

The compounds of the formula I are also suitable for use as an anisotropic, discotic matrix for spectroscopic investigations.

Other compounds having discotic properties and their use are described, for example, in U.S. Pat. No. 4,333,709. The use of the compounds of this invention is analogous.

Surprisingly, the compounds of the formula I proved to be discotic, liquid-crystal compounds which have in some cases, very wide meso ranges.

In addition, the provision of the compounds of the formula I broadens considerably, in a very general manner, the range of liquid-crystal substances which are suitable, from various aspects of application technology, for the preparation of discotic mixtures.

The compounds of the formula I, especially, for example, the thioethers of the formula I wherein at least one of the radicals $X^1$ to $X^6$ is —SR, are also suitable as intermediate products for the preparation of other substances, in particular, for example, the corresponding sulfones of the formula I, which can be used as constituents of liquid-crystal, discotic phases.

In the pure state, the compounds of the formula I are colorless and form liquid-crystal meso-phases within a temperature range which is advantageously situated for electrooptical use. They are very stable towards chemicals, heat and light.

The invention relates, therefore, to the compounds of the formula and to a process for their preparation, characterized in that ethers of the formula I wherein at least one of the radicals $X^1$ to $X^6$ is —OR are prepared by etherifying a corresponding hydroxy compound, and/or esters of the formula I wherein at least one of the radicals $X^1$ to $X^6$ is —COOR or —O—COR are prepared by esterifying a corresponding carboxylic acid, and/or thioethers of the formula I wherein at least one of the radicals $X^1$ to $X^6$ is —SR are prepared by reacting a corresponding halogen compound with a corresponding thiol or a salt thereof, and/or sulfoxides of the formula I wherein at least one of the radicals $X^1$ to $X^6$ is —SOR are prepared by oxidizing a corresponding thioether, and/or sulfones of the formula I wherein at least one of the radicals $X^1$ to $X^6$ is —SO$_2$R are prepared by oxidizing a corresponding thioether or a corresponding sulfoxide.

The invention also relates to the use of the compounds of the formula I as components of discotic, liquid-crystal phases. The invention also relates to discotic, liquid-crystal phases containing at least one compound of the formula I, and also to liquid-crystal display elements, containing phases of this type.

In the text which precedes and follows, A, $X^1$ to $X^6$ and R have the meaning indicated, unless anything to the contrary is expressly noted.

The compounds of the formula I accordingly embrace benzene derivatives of the partial formula Ia and cyclohexane derivatives of the partial formula Ib

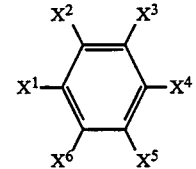

Ia

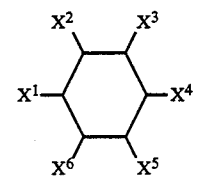

Ib

Preferred compunds of the formula I in which three of the radicals $X^1$ to $X^6$ are H, are the 1,3,5-trisubstituted compounds.

Preferred compounds of the formula I are those in which A is a cyclohexane ring.

Preferred compounds of the formula I are those in which none of the radicals $X^1$ to $X^6$ is H, in particular those in which the radicals $X^1$ to $X^6$ are identical and which correspond to the following partial formulae Ic to Im.

| Ph(OR)$_6$ | Ic | Cy(OR)$_6$ | Ih |
| Ph(COOR)$_6$ | Id | Cy(COOR)$_6$ | Ii |
| Ph(SR)$_6$ | Ie | Cy(SR)$_6$ | Ij |
| Ph(SOR)$_6$ | If | Cy(SOR)$_6$ | Ik |
| Ph(SO$_2$R)$_6$ | Ig | Cy(SO$_2$R)$_6$ | Il |
| | | Cy(O—COR)$_6$ | Im. |

The componds of the formulae Ig, Il and Im are preferred.

Moreover, preferred cyclohexanes of the formulae Ib and Ih to Im are those in which opposite substituents are in each case in the equatorial and trans-space positions in relation to one another. This corresponds to the configuration of scyllo-inositol.

Compounds of the formula I which contain one or more asymmetric C atoms can exist in a racemic or in an optically active form, both forms being covered by formula I.

R is an alkyl radical in which one (oxaalkyl) or two (dioxaalkyl) CH$_2$ groups can also be replaced by O atoms. These radicals can be linear or branched. Preferably, they are linear, have 3, 4, 5, 6, 7, 8, 9, 10, 11, 12 or 13 C atoms and accordingly are preferably propyl, butyl, pentyl, hexyl, heptyl, octyl, nonyl, decyl, undecyl, dodecyl, tridecyl, 2-oxapropyl (=methoxymethyl), 2-oxabutyl (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, and also ethyl, tetradecyl, pentadecyl, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8 or 9-oxadecyl, 2-, 3-, 4-, 5-, 6-, 7-, 8-, 9- and 10-oxaundecyl, 2-, 3-, 4-, 5-, 6-, 7-, 8-, 9-, 10- or 11- or oxadodecyl, 2-, 3-, 4-, 5-, 6-, 7-, 8-, 9-, 10- or 11- or 12-oxatridecyl, 2,4-dioxapentyl, 2,4-, 2,5- or 3,5-dioxahexyl, oxahexyl, 2,4-, 2,5-, 2,6-, 3,5-, 3,6- or 4,6-dioxaheptyl.

Compounds of the formulae I and also Ia to Im containing branched groups R can occasionally be important because of improved solubility in the customary liquid-crystal base materials, but can, in particular, be important as chiral doping substances if they are optically active. Branched groups of this type as a rule contain not more than one chain branching. Preferred branched radicals R are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, 2-oxa-3-methylbutyl, 3-oxa-4-methylpentyl.

Preferred compounds among the compounds of the formulae I and also Ia to Im are those in which the radical R has one of the preferred meanings indicated.

Compounds of the formula I are prepared by methods which are in themselves known, such as are described in the literature (for example in the standard works such as Houben-Weyl, *Methoden der Organischen Chemie* ("Methods of Organic Chemistry"), Georg-Thiem-Verlag, Stuttgart), under reaction conditions which are known and suitable for the reactions mentioned. In this respect it is also possible to utilize variants which are in themselves known but are not described here in more detail.

The starting materials are either known or can be prepared without difficulty by methods which are in themselves known analogously to known compounds. They can, if desired, also be formed in situ in a process in which they are not isolated from the reaction mixture, but are immediately reacted further to give the compounds of the formula I.

Ethers of the formula I (wherein at least one of the radicals $X^1$ to $X^6$ is OR), can be obtained by etherifying corresponding hydroxy compound, the hydroxy compound being preferably first converted into a corresponding metal derivative, for example into the corresponding alkali metal alcoholate or alkali metal phenolate by treatment with NaH, NaNH$_2$, NaOH, KOH, Na$_2$CO$_3$ or K$_2$CO$_3$. This derivative can then be reacted with the corresponding alkyl halide or sulfonate or dialkyl sulfate, preferably in an inert solvent, such as acetone, 1,2-dimethoxyethane, dimethylformamide (DMF) or dimethyl sulfoxide, or in an excess of aqueous or aqueous alcoholic NaOH or KOH at temperatures between about 20° and 100°.

Esters of the formula I wherein at least one of the radicals $X^1$ to $X^6$ is —COOR or —O—COR can be obtained by esterifying carboxylic acids which correspond to the formula I, but in which a COOH group is present instead of at least one of the radicals $X^1$ to $X^6$, with alcohols of the formula R-OH or by esterifying alcohols corresponding to the formula I in which A is a cyclohexane ring, but there is an OH group present instead of at least one of the radicals $X^1$ to $X^6$, with carboxylic acids of the formula R—COOH.

Instead of the carboxylic acids and/or alcohols, it is also possible to use reactive derivatives thereof.

Suitable reactive derivatives of the carboxylic acids mentioned are, in particular, the acid halides, above all the chlorides and bromides, and also the anhydrides, for example also mixed anhydrides, azides or esters, in particular alkyl esters having 1-4 C atoms in the alkyl group.

Suitable reactive derivatives of the alcohols mentioned are, in particular, the corresponding metal alcoholates wherein OM group(s) are present instead of the OH group(s) and wherein M is an equivalent of a metal, preferably an alkali metal, such as Na or K.

Esterification is advantageously carried out in the presence of an inert solvent. Solvents which are very suitable are, in particular, ethers, such as diethyl ether, di-n-butyl ether, THF, dioxane, or anisole, ketones, such as acetone, butanone or cyclohexanone, amides, such as DMF or phosphoric acid hexamethyltriamide, hydrocarbons, such as benzene, toluene or xylene, halogenated hydrocarbons, such as carbon tetrachloride or tetrachloroethylene, sulfoxides, such as dimethyl sulfoxide or sulfolane, and carboxylic acids, such as trifluoroacetic acid. Solvents which are not miscible with water can be used advantageously at the same time in order to remove, by azeotropic distillation, the water formed in the esterification. Occasionally, it is also possible to use an excess of an organic base, for example pyridine, quinoline or triethylamine, as the solvent for the esterification. The esterification can also be carried out in the absence of a solvent, for example merely by heating the components in the presence of sodium acetate. The reaction temperature is usually between −50° and +250°, preferably between −20° and +80°. At these temperatures, the esterification reactions are complete after 15 minutes to 48 hours, as a rule.

In an individual case, the reaction conditions for the esterification depend substantially on the nature of the starting materials used. Thus a free carboxylic acid is, as a rule, reacted with a free alcohol in the presence of a strong acid, for example a mineral acid, such as hydrochloric acid or sulfuric acid. A preferred mode of reaction is to react an acid anhydride or, in particular, an acid chloride with an alcohol, preferably in a basic medium, bases of importance being, in particular, alkali metal hydroxides, such as sodium hydroxide or potassium hydroxide, alkali metal carbonates or bicarbonates, such as sodium carbonate, sodium bicarbonate, potassium carbonate or potassium bicarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification reaction consists in first converting the alcohol into the sodium alcoholate or potassium alcoholate, for example by treatment with ethanolic sodium hydroxide solution or potassium hydroxide solution, isolating this alcoholate and suspending it, together with sodium bicarbonate or potassium carbonate, in acetone or diethyl ether, by stirring, and reacting this suspension with a solution of the acid chloride or anhydride in diethyl ether, acetone or DMF, preferably at temperatures between about $-25°$ and $+20°$.

Thioethers of the formula I wherein at least one of the radicals $X^1$ to $X^6$ is —SR, can be prepared by reacting a corresponding halogen compound, preferably a chlorine compound, such as hexachlorobenzene or hexachlorocyclohexane, with a corresponding thiol of the formula R—SH or, preferably, a salt thereof, especially the corresponding Na thiolate of the formula R—SNa. This reaction can be carried out in the presence or absence of an inert solvent, at temperatures between about $-20°$ and $250°$, preferably between $10°$ and $150°$. Examples of suitable solvents are hydrocarbons, such as benzene, toluene, xylenes or mesitylene; tertiary bases, such as triethylamine, pyridine or picolines; alcohols, such as methanol, ethanol or butanol; glycols and glycol ethers, such as ethylene glycol, diethylene glycol or 2-methoxyethanol; ketones, such as acetone; ethers, such as tetrahydrofuran or dioxane; amides, such as DMF or hexamethylphosphoric triamide (HMPT); or sulfoxides, such as dimethyl sulfoxide. Mixtures of these solvents are also suitable.

Sulfoxides and sulfones of the formula I wherein at least one of the radicals $X^1$ to $X^6$ is —SOR or —SO$_2$R can be prepared by oxidizing corresponding thioethers of the formula I wherein at least one of the radicals $X^1$ to $X^6$ is —SR.

Depending on the reagent chosen and on the conditions used, oxidation is carried out to give the corresponding sulfoxides (one of the groups $X^1$ to $X^6$=SO) or to give the corresponding sulfones (one of the groups $X^1$ to $X^6$=SO$_2$), the reaction being carried out by methods which are in themselves known from the literature, and the reaction conditions in an individual case being readily accessible in the literature. If it is desired to obtain the sulfoxides, oxidation is carried out, for example, by means of hydrogen peroxide, peracids, Cr(VI) compounds, such as chromic acid, nitric acid, nitrous gases, N$_2$O$_3$, halogens, such as chlorine, hypochlorites, KMnO$_4$, N-bromosuccinimide, 1-chlorobenztriazole, Ce(IV) compounds, such as (NH$_4$)$_2$Ce(NO$_3$)$_6$, or negatively substituted aromatic diazonium salts, such as o-nitrophenyldiazonium or p-nitrophenyldiazonium chloride, or electrolytically, under relatively mild conditions and at relatively low temperatures (about $-80°$ to $+100°$). If, on the other hand, it is desired to obtain the sulfones, the same oxidizing agents are used under more vigorous conditions and/or in excess and also, as a rule, at higher temperatures. The customary inert solvents can be present or absent in these reactions. Examples of suitable inert solvents are water, aqueous mineral acids, aqueous alkali metal hydroxide solutions, lower alcohols, such as methanol or ethanol, esters, such as ethyl acetate, ketones, such as acetone, lower carboxylic acids, such as acetic acid, nitriles, such as acetonitrile, hydrocarbons, such as benzene, or chlorinated hydrocarbons, such as chloroform or CCl$_4$.

A preferred oxidizing agent is 30% aqueous hydrogen peroxide. If the calculated quantity is used, in solvents such as acetic acid, acetone, ethanol or aqueous sodium hydroxide solution at temperatures between $-20°$ and $100°$, this results in the sulfoxides, while in excess, at higher temperatures, preferably in acetic acid or in a mixture of acetic acid and acetic anhydride, it results in the sulfones.

A further preferred oxidizing agent is 3-chloroperbenzoic acid. If the calculated amount is used, insolvents such as halogenated hydrocarbons at temperatures up to $0°$, this results in the sulfoxides, while in excess, at temperatures between $0°$ and room temperature, it results in the sulfones.

A further possible means of preparing the sulfoxides consists in treating the thioethers with chlorine, for example in moist benzene or in acetic acid. The dichloro compounds obtained intermediately are converted into the sulfoxides very readily by hydrolysis.

All of the starting material compounds used in the process of this invention are known and/or readily preparable from known compounds using fully conventional chemical reactions.

The discotic, liquid-crystal phases according to this invention comprise 2 to 15, preferably 3 to 12, components, including at least one compound of the formula I. The other constituents are preferably selected from the known discotic, liquid-crystal substances, in particular from the classes of hexa-substituted benzene or triphenylene derivatives. The phases according to the invention contain about 0.1 to 100, preferably 10 to 100% of one or more compounds of the formula I.

The preparation of the discotic, liquid-crystal phases according to the invention is effected in a manner which is in itself customary. As a rule, the components are dissolved in one another, preferably at an elevated temperature.

The discotic, liquid-crystal phases according to the invention can also be modified by means of suitable additives. For example, it is possible to add conductive salts in order to increase the conductivity, pleochroic dyestuffs or substances for varying the dielectric anisotropy, the viscosity and/or the alignment of the discotic phases.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid-crystal substance. "Customary working up" has the following meaning: water is added, the mixture is extracted with methylene chloride, the phases are separated, the organic phase is dried and evaporated and the product is purified by crystallization and/or chromatography.

EXAMPLE 1

A mixture of 17.4 g of hexahydroxybenzene, 150 g of hexyl iodide, 41.4 g of $K_2CO_3$ and 250 ml of DMF is heated at 80° for 16 hours, with stirring and is then cooled and worked up in the customary manner. This gives hexakis-(hexyloxy)-benzene.

The following are obtained analogously be etherifying hexahydroxy benzene or scyllo-inositol: Hexapropoxybenzene
Hexabutoxybenzene
Hexakis-(pentoxy)-benzene
Hexakis-(heptyloxy)-benzene
Hexakis-(octyloxy)-benzene
Hexakis-(nonyloxy)-benzene Hexakis-(decyloxy)-benzene
Hexakis-(undecyloxy)-benzene
Hexakis-(dodecyloxy)-benzene
Hexakis-(tridecyloxy)-benzene
Hexakis-(tetradecyloxy)-benzene
Hexakis-(pentadecyloxy)-benzene
scyllo-Inositol hexakis-(propyl ether)
scyllo-Inositol hexakis-(butyl ether)
scyllo-Inositol hexakis-(pentyl ether)
scyllo-Inositol hexakis-(hexyl ether)
scyllo-Inositol hexakis-(heptyl ether)
scyllo-Inositol hexakis-(octyl ether)
scyllo-Inositol hexakis-(nonyl ether)
scyllo-Inositol hexakis-(decyl ether)
scyllo-Inositol hexakis-(undecyl ether)
scyllo-Inositol hexakis-(dodecyl ether)
scyllo-Inositol hexakis-(tridecyl ether)
scyllo-Inositol hexakis-(tetradecyl ether)
scyllo-Inositol hexakis-(pentadecyl ether).

EXAMPLE 2

A mixture of 1.8 g of scyllo-inositol, 12 g of octanoyl chloride and 20 ml of trifluoroacetic acid is stirred for 2 hours at 20°. Evaporation and working up in the customary manner (elution with 20:1 hexane/ ethyl acetate) give hexakis-(octanoyl)-scyllo-inositol, m.p. 77.5°; c.p. 198.4°.

The following are obtained analogously using the corresponding acid chlorides:
Hexaacetylscyllo-inositol
Hexapropionylscyllo-inositol
Hexabutyrylscyllo-inositol
Hexaisobutyrylscyllo-inositol
Hexavalerylscyllo-inositol
Hexacapronylscyllo-inositol
Hexakis-(heptanoyl)-scyllo-inositol
Hexakis-(nonanoyl)-scyllo-inositol
Hexakis-(decanoyl)-scyllo-inositol
Hexakis-(undecanoyl)-scyllo-inositol
Hexakis-(dodecanoyl)-scyllo-inositol
Hexakis-(tridecanoyl)-scyllo-inositol
Hexakis-(tetradecanoyl)-scyllo-inositol
Hexakis-(pentadecanoyl)-scyllo-inositol.

EXAMPLE 3

3.48 g of scyllo-cyclohexane-1,2,3,4,5,6-hexacarboxylic acis are boiled for 1 hour with 14.4 g of $SOCl_2$, the mixture is evaporated, the resulting crude acid chloride is dissolved in 50 ml of toluene, 5 ml of pyridine and 10 g of heptanol are added and the mixture is boiled for 2 hours. Cooling and working up in the customary manner give hexakisheptyl scyllo-cyclohexane-1,2,3,4,5,6-hexacarboxylate.

The following are obtained analogously by esterification:
Hexamethyl scyllo-cyclohexane-1,2,3,4,5,6-hexacarboxylate
Hexaethyl scyllo-cyclohexane-1,2,3,4,5,6-hexacarboxylate
Hexapropyl scyllo-cyclohexane-1,2,3,4,5,6-hexacarboxylate
Hexabutyl scyllo-cyclohexane-1,2,3,4,5,6-hexacarboxylate
Hexakispentyl scyllo-cyclohexane-1,2,3,4,5,6-hexacarboxylate
Hexakishexyl scyllo-cyclohexane-1,2,3,4,5,6-hexacarboxylate
Hexakisoctyl scyllo-cyclohexane-1,2,3,4,5,6-hexacarboxylate
Hexakisnonyl scyllo-cyclohexane-1,2,3,4,5,6-hexacarboxylate
Hexakisdecyl scyllo-cyclohexane-1,2,3,4,5,6-hexacarboxylate
Hexakisundecyl scyllo-cyclohexane-1,2,3,4,5,6-hesacarboxylate
Hexakisdodecyl scyllo-cyclohexane-1,2,3,4,5,6-hexacarboxylate
Hexakistridecyl scyllo-cyclohexane-1,2,3,4,5,6-hexacarboxylate
Hexakistetradecyl scyllo-cyclohexane-1,2,3,4,5,6-hexacarboxylate
Hexakispentadecyl scyllo-cyclohexane-1,2,3,4,5,6-hexacarboxylate
Hexamethyl mellitate
Hexaethyl mellitate
Hexapropyl mellitate
Hexabutyl mellitate
Hexakispentyl mellitate
Hexakishexyl mellitate
Hexakisheptyl mellitate
Hexakisoctyl mellitate
Hexakisnonyl mellitate
Hexakisdecyl mellitate
Hexakisundecyl mellitate
Hexakisdodecyl mellitate
Hexakistridecyl mellitate
Hexakistetradecyl mellitate
Hexakispentadecyl mellitate.

EXAMPLE 4

A mixture of 2.85 g of hexachlorobenzene, 21.8 g of sodium nonylthiolate and 100 ml of HMPT is stirred for 10 hours at 20° under $N_2$ and is evaporated and worked up in the customary manner ($Al_2O_3$; 94:6 petroleum ether/ether) to give hexakis-(nonylthio)-benzene, an oil, no boiling point below 250°/0.1 mmHg.

The following are obtained analogously from hexachlorobenzene or β-hexachlorocyclohexane:
Hexakis-(methylthio)-benzene
Hexakis-(ethylthio)-benzene
Hexakis-(propylthio)-benzene Hexakis-(butylthio)-benzene
Hexakis-(pentylthio)-benzene
Hexakis-(hexylthio)-benzene
Hexakis-(heptylthio)-benzene
Hexakis-(octylthio)-benzene
Hexakis-(decylthio)-benzene
Hexakis-(undecylthio)-benzene, m.p. 29°–30°
Hexakis-(dodecylthio)-benzene
Hexakis-(tridecylthio)-benzene, m.p. 44°–45°
Hexakis-(tetradecylthio)-benzene
Hexakis-(pentadecylthio)-benzene
scyllo-1,2,3,4,5,6-Hexakis-(methylthio)-cyclohexane
scyllo-1,2,3,4,5,6-Hexakis-(ethylthio)-cyclohexane
scyllo-1,2,3,4,5,6-Hexakis-(propylthio)-cyclohexane
scyllo-1,2,3,4,5,6-Hexakis-(butylthio)-cyclohexane
scyllo-1,2,3,4,5,6-Hexakis (pentylthio)-cyclohexane
scyllo-1,2,3,4,5,6-Hexakis-(hexylthio)-cyclohexane
scyllo-1,2,3,4,5,6-Hexakis-(heptylthio)-cyclohexane
scyllo-1,2,3,4,5,6-Hexakis-(octylthio)-cyclohexane
scyllo-1,2,3,4,5,6-Hexakis-(nonylthio)-cyclohexane
scyllo-1,2,3,4,5,6-Hexakis-(decylthio)-cyclohexane
scyllo-1,2,3,4,5,6-Hexakis-(undecylthio)-cyclohexane
scyllo-1,2,3,4,5,6-Hexakis-(dodecylthio)-cyclohexane
scyllo-1,2,3,4,5,6-Hexakis-(tridecylthio)-cyclohexane
scyllo-1,2,3,4,5,6-Hexakis-(tetradecylthio)-cyclohexane
scyllo-1,2,3,4,5,6-Hexakis-(pentadecylthio)-cyclohexane

EXAMPLE 5

A solution of 6.42 ml of 30% $H_2O_2$ in 150 ml of acetic acid is added dropwise to a solution of 10.26 g of hexakis-(nonylthio)-benzene in 400 ml of acetic acid at 75°–80° in the course of 30 minutes and with stirring. The mixture is kept at 80° for 2 hours, boiled up and poured into water, and working up in the customary manner gives hexakis-(nonylsulfinyl)-benzene.

The following are obtained analogously by oxidizing the corresponding thioethers:
Hexakis-(methylsulfinyl)-benzene
Hexakis-(ethylsulfinyl)-benzene
Hexakis-(propylsulfinyl)-benzene
Hexakis-(butylsulfinyl)-benzene
Hexakis-(pentylsulfinyl)-benzene
Hexakis-(hexylsulfinyl)-benzene
Hexakis-(heptylsulfinyl)-benzene
Hexakis-(octylsulfinyl)-benzene
Hexakis-(decylsulfinyl)-benzene
Hexakis-(undecylsulfinyl)-benzene
Hexakis-(dodecylsulfinyl)-benzene
Hexakis-(tridecylsulfinyl)-benzene
Hexakis-(tetradecylsulfinyl)-benzene
Hexakis-(pentadecylsulfinyl)-benzene
scyllo-1,2,3,4,5,6-Hexakis-(methylsulfinyl)-cyclohexane
scyllo-1,2,3,4,5,6-Hexakis-(ethylsulfinyl)-cyclohexane
scyllo-1,2,3,4,5,6-Hexakis-(propylsulfinyl)-cyclohexane
scyllo-1,2,3,4,5,6-Hexakis-(butylsulfinyl)-cyclohexane
scyllo-1,2,3,4,5,6-Hexakis-(pentylsulfinyl)-cyclohexane
scyllo-1,2,3,4,5,6-Hexakis-(hexylsulfinyl)-cyclohexane
scyllo-1,2,3,4,5,6-Hexakis-(heptylsulfinyl)-cyclohexane
scyllo-1,2,3,4,5,6-Hexakis-(octylsulfinyl)-cyclohexane
scyllo-1,2,3,4,5,6-Hexakis-(nonylsulfinyl)-cyclohexane
scyllo-1,2,3,4,5,6-Hexakis-(decylsulfinyl)-cyclohexane
scyllo-1,2,3,4,5,6-Hexakis-(undecylsulfinyl)-cyclohexane
scyllo-1,2,3,4,5,6-Hexakis-(dodecylsulfinyl)-cyclohexane
scyllo-1,2,3,4,5,6-Hexakis-(tridecylsulfinyl)-cyclohexane
scyllo-1,2,3,4,5,6-Hexakis-(tetradecylsulfinyl)-cyclohexane
scyllo-1,2,3,4,5,6-Hexakis-(pentadecylsulfinyl)-cyclohexane.

EXAMPLE 6

10.26 g of hexakis-(nonylthio)-benzene are boiled for 48 hours with a 20% excess of 85–90% m-chloroperbenzoic acid in a total of 60 ml of $CHCl_3$, the mixture is evaporated and the residue is recrystallized from ethanol/petroleum ether to give hexakis-(nonylsulfonyl)-benzene, m.p. 95°, c.p. 131°.

The following are obtained analogously by oxidizing the corresponding thioethers:
Hexakis-(methylsulfonyl)-benzene
Hexakis-(ethylsulfonyl)-benzene
Hexakis-(propylsulfonyl)-benzene
Hexakis-(butylsulfonyl)-benzene
Hexakis-(pentylsulfonyl)-benzene
Hexakis-(hexylsulfonyl)-benzene
Hexakis-(heptylsulfonyl)-benzene
Hexakis-(octylsulfonyl)-benzene
Hexakis-(decylsulfonyl)-benzene
Hexakis-(undecylsulfonyl)-benzene, m.p. 76°, c.p. 116°
Hexakis-(dodecylsulfonyl)-benzene
Hexakis-(tridecylsulfonyl)-benzene, m.p. 60°, c.p. 89°
Hexakis-(tetradecylsulfonyl)-benzene
Hexakis-(pentadecylsulfonyl)-benzene
scyllo-1,2,3,4,5,6-Hexakis-(methylsulfonyl)-cyclohexane
scyllo-1,2,3,4,5,6-Hexakis-(ethylsulfonyl)-cyclohexane
scyllo-1,2,3,4,5,6-Hexakis-(propylsulfonyl)-cyclohexane
scyllo-1,2,3,4,5,6-Hexakis-(butylsulfonyl)-cyclohexane
scyllo-1,2,3,4,5,6-Hexakis-(pentylsulonyl)-cyclohexane
scyllo-1,2,3,4,5,6-Hexakis-(hexylsulfonyl)-cyclohexane
scyllo-1,2,3,4,5,6-Hexakis-(heptylsulfonyl)-cyclohexane
scyllo-1,2,3,4,5,6-Hexakis-(octylsulfonyl)-cyclohexane
scyllo-1,2,3,4,5,6-Hexakis-(nonylsulfonyl)-cyclohexane
scyllo-1,2,3,4,5,6-Hexakis-(decylsulfonyl)-cyclohexane
scyllo-1,2,3,4,5,6-Hexakis-(undecylsulfonyl)-cyclohexane
scyllo-1,2,3,4,5,6-Hexakis-(dodecylsulfonyl)-cyclohexane
scyllo-1,2,3,4,5,6-Hexakis-(tridecylsulfonyl)-cyclohexane
scyllo-1,2,3,4,5,6-Hexakis-(tetradecylsulfonyl)-cyclohexane
scyllo-1,2,3,4,5,6-Hexakis-(pentadecylsulfonyl)-cyclohexane.
1,3,5-Tris-(propylsulfonyl)-benzene
1,3,5-Tris-(butylsulfonyl)-benzene
1,3,5-Tris-(pentylsulfonyl)-benzene
1,3,5-Tris-(hexylsulfonyl)-benzene
1,3,5-Tris-(heptylsulfonyl)-benzene
1,3,5-Tris-(octylsulfonyl)-benzene
1,3,5-Tris-(nonylsulfonyl)-benzene
1,3,5-Tris-(decylsulfonyl)-benzene
1,3,5-Tris-(undecylsulfonyl)-benzene
1,3,5-Tris-(dodecylsulfonyl)-benzene
1,3,5-Tris-(tridecylsulfonyl)-benzene
1,3,5-Tris-(tetradecylsulfonyl)-benzene
1,3,5-Tris-(pentadecylsulfonyl)-benzene
1,2,3,5-Tetrakis-(propylsulfonyl)-benzene
1,2,3,5-Tetrakis-(butylsulfonyl)-benzene
1,2,3,5-Tetrakis-(pentylsulfonyl)-benzene
1,2,3,5-Tetrakis-(hexylsulfonyl)-benzene
1,2,3,5-Tetrakis-(heptylsulfonyl)-benzene 1,2,3,5-Tetrakis-(octylsulfonyl)-benzene
1,2,3,5-Tetrakis-(nonylsulfonyl)-benzene
1,2,3,5-Tetrakis-(decylsulfonyl)-benzene
1,2,3,5-Tetrakis-(undecylsulfonyl)-benzene
1,2,3,5-Tetrakis-(dodecylsulfonyl)-benzene
1,2,3,5-Tetrakis-(tridecylsulfonyl)-benzene
1,2,3,5-Tetrakis-(tetradecylsulfonyl)-benzene
1,2,3,5-Tetrakis-(pentadecylsulfonyl)-benzene
r-1, c-3, c-5-Tris-(propylsulfonyl)-cyclohexane
r-1, c-3, c-5-Tris-(butylsulfonyl)-cyclohexane
r-1, c-3, c-5-Tris-(pentylsulfonyl)-cyclohexane
r-1, c-3, c-5-Tris-(hexylsulfonyl)-cyclohexane
r-1, c-3, c-5-Tris-(heptylsulfonyl)-cyclohexane
r-1, c-3, c-5-Tris-(octylsulfonyl)-cyclohexane
r-1, c-3, c-5-Tris-(nonylsulfonyl)-cyclohexane
r-1, c-3, c-5-Tris-(decylsulfonyl)-cyclohexane
r-1, c-3, c-5-Tris-(undecylsulfonyl)-cyclohexane
r-1, c-3, c-5-Tris-(dodecylsulfonyl)-cyclohexane
r-1, c-3, c-5-Tris-(tridecylsulfonyl)-cyclohexane
r-1, c-3, c-5-Tris-(tetradecylsulfonyl)-cyclohexane
r-1, c-3, c-5-Tris-(pentadecylsulfonyl)-cyclohexane.

EXAMPLE 7

A mixture of 0.9 g of scyllo-inositol pentakis-(nonyl ether), 0.2 g of octanoyl chloride and 10 ml of triflurora-cetic acid is stirred at room temperature for 2 hours. Evaporating the mixture and working up the residue in the customary manner give octanoyl-scyllo-inositol pentakis-(nonyl ether).

The following are obtained analogously using the corresponding acid chlorides:
Propionyl-scyllo-inositol pentakis-(nonyl ether)
Butyryl-scyllo-inositol pentakis-(nonyl ether)
Valeryl-scyllo-inositol pentakis-(nonyl ether)
Capronyl-scyllo-inositol pentakis-(nonyl ether)
Heptanoyl-scyllo-inositol pentakis-(nonyl ether)
Nonanoyl-scyllo-inositol pentakis-(nonyl ether)
Undecanoyl-scyllo-inositol pentakis-(nonyl ether)
Dodecanoyl-scyllo-inositol pentakis-(nonyl ether)
Tridecanoyl-scyllo-inositol pentakis-(nonyl ether)
Tetradecanoyl-scyllo-inositol pentakis-(nonyl ether)
Pentadecanoyl-scyllo-inositol pentakis-(nonyl ether).

EXAMPLE 8

A mixture of 1.8 g of 1,3,5-trichlorobenzene, 10.9 g of sodium nonylthiolate and 50 ml of HMPT is stirred for 10 hours at 20° under $N_2$ and is evaporated and worked up in the customary manner to give 1,3,5-tris-(nonylthio)-benzene.

The following are obtained analogously from 1,3,5-trichlorobenzene, 1,2,3,5-tetracholrobenzene or r-1, c-3, c-5-trichlorocyclohexane:
1,3,5-Tris-(propylthio)-benzene
1,3,5-Tris-(butylthio)-benzene
1,3,5-Tris-(pentylthio)-benzene
1,3,5-Tris-(hexylthio)-benzene
1,3,5-Tris-(heptylthio)-benzene
1,3,5-Tris-(octylthio)-benzene
1,3,5-Tris-(nonylthio)-benzene
1,3,5-Tris-(decylthio)-benzene
1,3,5-Tris-(undecylthio)-benzene
1,3,5-Tris-(dodecylthio)-benzene
1,3,5-Tris-(tridecylthio)-benzene
1,3,5-Tris-(tetradecylthio)-benzene
1,3,5-Tris-(pentadecylthio)-benzene
1,2,3,5-Tetrakis-(propylthio)-benzene
1,2,3,5-Tetrakis-(butylthio)-benzene
1,2,3,5-Tetrakis-(pentylthio)-benzene
1,2,3,5-Tetrakis-(hexylthio)-benzene
1,2,3,5-Tetrakis-(heptylthio)-benzene
1,2,3,5-Tetrakis-(octylthio)-benzene
1,2,3,5-Tetrakis-(nonylthio)-benzene
1,2,3,5-Tetrakis-(decylthio)-benzene
1,2,3,5-Tetrakis-(undecylthio)-benzene
1,2,3,5-Tetrakis-(dodecylthio)-benzene
1,2,3,5-Tetrakis-(tridecylthio)-benzene
1,2,3,5-Tetrakis-(tetradecylthio)-benzene
1,2,3,5-Tetrakis-(pentadecylthio)-benzene
r-1, c-3, c-5-Tris-(propylthio)-cyclohexane
r-1, c-3, c-5-Tris-(butylthio)-cyclohexane
r-1, c-3, c-5-Tris-(pentylthio)-cyclohexane
r-1, c-3, c-5-Tris-(hexylthio)-cyclohexane
r-1, c-3, c-5-Tris-(heptylthio)-cyclohexane
r-1, c-3, c-5-Tris-(octylthio)-cyclohexane
r-1, c-3, c-5-Tris-(nonylthio)-cyclohexane
r-1, c-3, c-5-Tris-(decylthio)-cyclohexane
r-1, c-3, c-5-Tris-(undecylthio)-cyclohexane
r-1, c-3, c-5-Tris-(dodecylthio)-cyclohexane
r-1, c-3, c-5-Tris-(tridecylthio)-cyclohexane
r-1, c-3, c-5-Tris-(tetradecylthio)-cyclohexane
r-1, c-3, c-5-Tris-(pentadecylthio)-cyclohexane.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A discotic, liquid-crystal phase containing at least two liquid-crystal components, wherein at least one of said components is

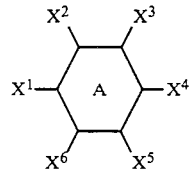

wherein
A is a benzene or cyclohexane ring,
$X^1$ to $X^6$ independently of one another in each case are H, —OR, —COOR, —SR, —SOR, or —$SO_2$R or, when A is a cyclohexane ring, also —O—COR, and
R is in each case alkyl of up to 15 C atoms or alkyl of up to 15 C-atoms wherein one or two $CH_2$ groups are replaced by O atoms,
at least three of the substituents $X^1$ to $X^6$ being other than H.

2. A liquid-crystal phase of claim 1, wherein A is benzene.

3. A liquid-crystal phase of claim 1, wherein A is cyclohexane.

4. A liquid-crystal phase of claim 1, wherein three of $X^1$ to $X^6$ are not H and they are in the 1-, 3-, and 5-positions.

5. A liquid-crystal phase of claim 1, wherein none of $X^1$ to $X^6$ is H.

6. A liquid-crystal phase of claim 5, wherein all of $X^1$ to $X^6$ are the same.

7. A liquid-crystal phase of claim 6, of the formulae Ph(SO$_2$R)$_6$, Cy(SO$_2$R)$_6$ or Cy(O—COR)$_6$, wherein Ph is a benzene ring and Cy is a cylcohexane ring.

8. A liquid-crystal phase of claim 3, wherein opposite substituents are in the equatorial and transspace positions relative to one another.

9. A liquid-crystal phase of claim 3, wherein said compound is hexaoctanoylscyllo-inositol, hexakis-(nonylsulfonyl)-benzene, hexakis-(undecylsulfonyl)-benzene, or hexakis-(tridecylsulfonyl)-benzene.

10. In a liquid-crystal electro-optical display element comprising a liquid-crystal phase, the improvement wherein the phase is one of claim 1.

* * * * *